United States Patent [19]

Tsuda et al.

[11] 4,416,982
[45] Nov. 22, 1983

[54] COMPOSITION AND METHOD FOR DECOMPOSING HYDROGEN PEROXIDE

[75] Inventors: Mitsuru Tsuda, Mishima; Akira Miike; Yoshiaki Shimizu, both of Shizuoka; Yasuharu Yokote, Tokyo; Toshio Tatano, Numazu, all of Japan

[73] Assignee: Kyowa Hakko Kogyo Co., Ltd., Tokyo, Japan

[21] Appl. No.: 321,603

[22] Filed: Nov. 16, 1981

[30] Foreign Application Priority Data

Nov. 14, 1980 [JP] Japan ................. 55-159403

[51] Int. Cl.$^3$ ............ C12Q 1/60; C12Q 1/54; C12Q 1/52; C12Q 1/44; C12Q 1/42; C12Q 1/40; C12Q 1/26; C12Q 1/28; C12Q 1/00
[52] U.S. Cl. ............ 435/11; 435/14; 435/16; 435/19; 435/21; 435/22; 435/4; 435/25; 435/28
[58] Field of Search ............ 435/11, 14, 16, 19, 435/21, 22, 25, 28, 4

[56] References Cited

U.S. PATENT DOCUMENTS

| | | | |
|---|---|---|---|
| 3,886,045 | 5/1975 | Meiattini | 435/14 |
| 4,086,142 | 4/1978 | Huang et al. | 435/16 |
| 4,172,765 | 10/1979 | Keyes | 435/22 |
| 4,186,251 | 1/1980 | Tarbutton | 435/11 |
| 4,242,446 | 12/1980 | Madappally et al. | 435/16 |
| 4,251,629 | 2/1981 | Yamanisi | 435/28 |
| 4,291,121 | 9/1981 | Acquati et al. | 435/28 |
| 4,309,502 | 1/1982 | Lauderdale | 435/19 |
| 4,316,954 | 2/1982 | Snoke et al. | 435/25 |

FOREIGN PATENT DOCUMENTS 7787 2/1980 European Pat. off.
1186668 4/1970 United Kingdom.

OTHER PUBLICATIONS

Proelss et al, Clin. Chem., 21(6), 694–702 (1975).

Primary Examiner—Esther M. Kepplinger
Attorney, Agent, or Firm—Antonelli, Terry & Wands

[57] ABSTRACT

A method for decomposing hydrogen peroxide is disclosed. The hydrogen peroxide is reacted with a compound represented by the formula (I)

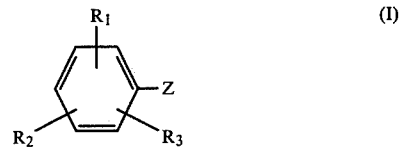

wherein Z represents OH or $NR_4.R_5$ wherein $R_4$ and $R_5$ are the same or different and represent hydrogen, alkyl, substituted alkyl or acyl, and $R_1, R_2$ and $R_3$ are the same or different and represent hydrogen, halogen, alkyl, alkoxy, amino, nitro, carboxyl or sulphonyl, in the presence of peroxidase.

9 Claims, No Drawings

COMPOSITION AND METHOD FOR DECOMPOSING HYDROGEN PEROXIDE

BACKGROUND OF THE INVENTION

The present invention relates to a method for decomposing hydrogen peroxide in a sample and more particularly, to a method for decomposing hydrogen peroxide by reacting the hydrogen peroxide with phenol, aniline or derivatives thereof in the presence of peroxidase.

Hydrogen peroxide is useful as bleaching agent for food, etc. and catalase is usually used for decomposing the hydrogen peroxide remaining in the sample. However, according to the prior method, the rate of decomposition is slow and a small amount of hydrogen peroxide remains in a sample. Therefore, an excellent method for decomposing hydrogen peroxide is in demand.

SUMMARY OF THE INVENTION

It has been found that the reaction of hydrogen peroxide with a compound represented by the formula (I) below [hereinafter referred to as Compound (I)] proceeds rapidly in the presence of peroxidase, whereby hydrogen peroxide is completely decomposed.

Formula (I):

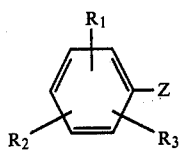

In the above formula, Z is OH or $NR_4R_5$ wherein $R_4$ and $R_5$ are the same or different and represent hydrogen atom, alkyl, substituted alkyl or acyl, and $R_1$, $R_2$ and $R_3$ are the same or different and represent hydrogen atom, halogen atom, alkyl, alkoxy, amino, nitro, carboxyl or sulfonyl.

As used herein, alkyl means alkyl having 1–5 carbon atoms such as methyl, ethyl, propyl, butyl and pentyl. Substituents of substituted alkyl include hydroxyl, amino and acylamino and acyl in acylamino has the same significance as that in $R_4$. Acyl means acyl having 1–5 carbon atoms such as formyl, acetyl, propionyl and butyryl. Alkoxy means alkoxy having 1–5 carbon atoms such as methoxy, The principle of the present invention can be applied to the determination of a compound or a substance to be analyzed (hereinafter referred to as analyte) such as cholesterol ester in serum and the determination can be easily carried out in a short period of time. Heretofore, it is known that the determination of the substrate for an oxidase is conducted by oxidizing the substrate by the action of the oxidase and determining the amount of reaction product stoichiometrically formed. In the case where hydrogen peroxide is formed as a reaction product, the determination of hydrogen peroxide is usually carried out by adding a chromogen and peroxidase to the enzymatic reaction mixture to form a pigment and measuring the absorbance of the reaction solution colored by the formation of pigment.

When the analyte to be determined is not directly oxidized by an oxidase, the analyte is converted to the compound which can be directly oxidized by the oxidase and the compound is determined by the known method described above.

However if the sample contains both of the analyte and the compound, the compound must be removed or decomposed prior to the determination of the analyte. When the removal or decomposition is difficult, the determination of the analyte is performed by determining the total amount and the amount of the compound in the original sample and calculating the difference of the results.

For example, for the determination of ester form of a compound in a sample containing ester form of the compound and free form of the compound, usually, first the free form is determined by oxidizing the free form with oxidase capable of oxidizing the compound to form hydrogen peroxide and determining the hydrogen peroxide formed. Then, ester form in an original sample is converted to free form by suitable means such as by using esterase capable of hydrolizing the compound or by alkali hydrolysis, and total of the free form formed and contained in the original sample is determined according to the determination method of the free form described above. Thus the amount of ester form is calculated from the difference of total content and free form content.

In this case, the ester form is easily determined by applying the present method. That is, the free form in the sample is oxidized by the action of oxidase capable of oxidizing the free form compound to form hydrogen peroxide which is then reacted with Compound (I) in the presence of peroxidase to form non-coloring compound. The ester form in the reaction mixture is converted to free form with esterase capable of hydrolyzing the ester form and the resulting free form is oxidized with the oxidase to form hydrogen peroxide which is then reacted with chromogen in the presence of peroxidase to form a pigment. The hydrogen peroxide is determined by measuring the absorbancy of the reaction solution colored by the formulation of a pigment.

The principle of the present method can be applied not only to the determination of ester form compound in a sample containing ester form and free form, but also to the decomposition of hydrogen peroxide derived from the compound not to be determined.

DESCRIPTION OF THE INVENTION

Examples of the Compound (I) include phenol, 2,4-dichlorophenol, p-chlorophenol, 2,4-dibromophenol, p-bromophenol, 2,3-dichlorophenol, 2-nitrophenol, 3-nitrophenol, 2-aminophenol, 3-aminophenol, aniline, 2-bromoaniline, 3-bromoaniline, 2-chloroaniline, 3-chloroaniline, o-toluidine, m-toluidine, dimethylaniline, diethylaniline, o-phenylenediamine, N,N-p-phenylenediamine, o-anisidine, m-anisidine, N-ethyl-N-(3-methylphenyl)-N'-acetylethylenediamine, o-cresol, m-cresol, 2-methyl-2,6-dinitrophenol, 2-methoxy-5-nitroaniline, 2-methyl-5-nitroaniline, 3,5-dihydroxytoluene, 3-methoxyphenol, 2-amino-5-methylphenol, 2-hydroxy-3-methylbenzoic acid, 2-hydroxyphenylacetic acid, 2,3-dimethylphenol, 2,5-dimethylphenol, 2-ethylphenol, 3-ethylphenol, 2-methoxymethylphenol, 2,3-dimethylaniline, 2,5-dimethylaniline, 3,5-diethylaniline, 3-(dimethylamino)phenol, 3-methoxy-N,N-dimethylaniline, N,N-diethyl-1,3-phenylenediamine, and 3,5-dimethyl-1,2-phenylenediamine.

In decomposing hydrogen peroxide according to the present invention, at least equimolar amount, usually 10–100 times amount of Compound (I) to that of hydrogen peroxide to be decomposed is added to the sample, and peroxidase is used in a concentration of 1–30 U/ml.

The reaction is carried out at a temperature of 0°–50° C. and at a pH of 2–10 in an aqueous solution and is completed in 60 seconds, usually in 10 seconds.

The mechanism of the reaction is not clear, but as is shown in the following experiment, it is obvious that hydrogen peroxide is completely decomposed in a short period of time.

EXPERIMENT

The decomposition time of hydrogen peroxide by the reaction of hydrogen peroxide with Compound (I) is measured by the following method.

Good buffer solutions having various pH are prepared. To 3 ml of the buffer solutions are added 30 mg of Triton X-100, 40 U of peroxidase and 0.9 mg of Compound (I) indicated in Table 1 to make test solutions. Then 0.06 μl of hydrogen peroxide solution is added to the test solution and the mixture is incubated at 37° C. with shaking. To monitor the presence of hydrogen peroxide in the mixture, 0.3 mg of 4-AA is added.

4-AA reacts with Compound (I) and hydrogen peroxide in the presence of peroxidase to form a pigment, and the reaction solution is colored. The development of color does not occur if hydrogen peroxide is completely decomposed, and therefore, the completion of the reaction is confirmed by the addition of 4-AA.

TABLE 1

| Compound No. | Compound (I) | Time (second) pH5 | 6 | 6.75 | 8 |
|---|---|---|---|---|---|
| 1 | (3-CH3-phenyl)-N(C2H5)(C2H4NHCOCH3) | 4 | 4 | 5 | 5 |
| 2 | phenyl-N(CH3)2 | " | " | 6 | 7 |
| 3 | phenyl-N(C2H5)2 | " | " | " | " |
| 4 | 3-OCH3-phenyl-N(C2H5)2 | " | " | " | 10 |
| 5 | (2-NH2, 3-CH3, 5-OCH3-phenyl)-N(CH3)2 | " | " | " | 5 |
| 6 | (2-Br, 5-COCH3-phenyl)-NH2 | " | " | " | 6 |
| 7 | Cl-phenyl-OH | 15 | 15 | 10 | 10 |
| 8 | (Cl, Cl-phenyl)-OH | " | " | " | " |
| 9 | (Br, Br-phenyl)-OH | " | " | " | " |
| 10 | phenyl-OH | " | " | " | " |
| 11 | (Cl, CH3, Cl-phenyl)-OH | 25 | 20 | 20 | 20 |
| 12 | (3-CH3-phenyl)-OH | 14 | 14 | 13 | 10 |
| 13 | (Cl, C2H5-phenyl)-OH | 35 | 30 | 30 | 25 |
| 14 | (Cl, C2H5-phenyl)-N(C2H5)2 | 4 | 5 | 5 | 6 |
| 15 | 4-AA | 300 | 300 | 350 | 440 |

The colorimetry is carried out at 550 nm in utilization of aniline compound and at 500 nm in utilization of phenol compound. The time required to complete the reaction is shown in Table 1.

For comparison, the same procedures as described above are repeated except that 4-AA is used instead of Compound (I) and phenol is used for monitoring the completion of reaction.

The present method can be applied to the determination of analytes such as cholesterol ester in a sample containing free form and ester form of cholesterol, triglyceride in a sample containing free form and ester form of glycerol, phospholipid (containing choline) in a sample containing free form of choline and phospholipid, sialo-compound and creatinine, and enzyme activity such as α-amylase activity and transaminase activity.

The reactions for the determination of the analytes are illustrated as follows.

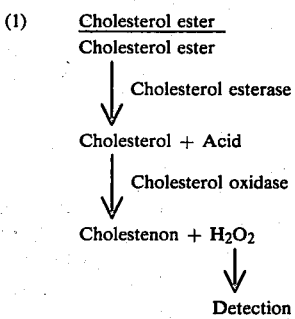

(1) Cholesterol ester

Cholesterol ester
↓ Cholesterol esterase
Cholesterol + Acid
↓ Cholesterol oxidase
Cholestenon + $H_2O_2$
↓
Detection -continued (2) Triglyceride Triglyceride
↓ Lipoprotein lipase
Glycerol + Fatty acid
↓ Glycerol oxidase
Glyceraldehyde + $H_2O_2$
↓
Detection (3) Phospholipid Phospholipid
↓ Phospholipase D
Choline
↓ Choline oxidase
Choline aldehyde + $H_2O_2$
↓
Detection (4) Transaminase activity Glutamate oxaloacetate transaminase (GOT)
Glutamate pyruvate transaminase (GPT)

(GPT)

L-Alanine + α-Ketoglutaric acid
↓ GPT
Pyruvic acid + L-Glutamic acid
↓ Pyruvate oxidase and phosphate
Acetyl phosphate + $CO_2$ + $H_2O_2$
↓
Detection (GOT)

L-Aspartic acid + α-Ketoglutaric acid
↓ GOT
Oxaloacetic acid + L-Glutamic acid
↓ Oxaloacetate decarboxylase
Pyruvic acid + $CO_2$
↓ Pyruvate oxidase and phosphate
Acetyl phosphate + $CO_2$ + $H_2O_2$
↓
Detection (5) α-Amylase activity -continued Starch
↓ α-Amylase
Maltose
↓ α-Glucosidase
Glucose
↓ Glucose oxidase or Pyranose oxidase
Gluconic acid + $H_2O_2$
↓
Detection (6) Sialocompound Sialocompound
↓ Neuraminidase
N—acetylneuraminic acid + Asialocompound
↓ N—Acetylneuraminic acid aldolase
Pyruvic acid + N—acetylmannosamine
↓ Pyruvate oxidase
Acetylphosphate + $H_2O_2$
↓
Detection (7) Creatinine Creatinine
↓ Creatininase
Creatine + $H_2O$
↓ Creatinase
Urea + Sarcosine
↓ Sarcosine oxidase
Formaldehyde + Glycine + $H_2O_2$
↓
Detection In the determination of the analytes or the enzyme activity described above, when cholesterol, glycerol, choline, pyruvic acid, maltose, glucose, creatine or the like is contained in a sample, the determination is inhibited by the presence of such compound in the sample. Therefore, the compound is decomposed prior to the determination of the analyte.

In the determination of the analyte in a sample, the analyte is converted to a compound [compound (A)] which is directly oxidized by the action of an oxidase [oxidase (A)] and the compound (A) is determined by the known method described above.

The determination of the analyte in a sample containing compound (A) is carried out as follows.

(1) Oxidase (A), Compound (I) and peroxidase are added to the sample to oxidize Compound (A) in a sample to form hydrogen peroxide which is then decomposed to form non-coloring compound.

(2) The enzyme capable of converting the analyte to Compound (A) [enzyme (B)] and chromogen are added to the reaction mixture to form a pigment.

(3) The absorbancy of the reaction mixture is measured in the visible ray region.

In the determination of an enzyme activity, the substrate for the enzyme added to the sample is converted to a compound [compound (A)] which is directly oxidized by the action of an oxidase [oxidase (A)] and compound (A) is determined by the known method.

The determination of the enzyme activity in a sample containing compound (A) is carried out as follows.

(1) Oxidase (A), Compound (I) and peroxidase are added to the sample to oxidize Compound (A) in the sample to form hydrogen peroxide which is then decomposed to form non-coloring compound.

(2) The substrate for the enzyme and chromogen are added to the reaction mixture to form a pigment.

(3) The absorbancy of the reaction mixture is measured in the visible ray region.

As the chromogen used in the present invention, any chromogen may be used so long as it reacts with hydrogen peroxide in the presence of peroxidase to form stoichiometrically a pigment.

Compound (I) may be used as a part of chromogen. In this case, Compound (I) of aniline group is used in combination with phenol and Compound (I) of phenol group is used in combination with 4-AA.

When compound (I) is not used as a part of chromogen. The rate of the reaction of hydrogen peroxide with the chromogen added must be faster than that of hydrogen peroxide with Compound (I) utilized.

Examples of the chromogen include 4-aminoantipyrine (hereinafter referred to as "4-AA") and N-ethyl-N-($\beta$-hydroxyethyl)-m-toluidine, 3-methyl-2-thiazolinone hydrazone (hereinafter referred to as MBTH) and o-toluidine, MBTH and N,N-dimethylaniline, o-dianisidine and 4,4',4''-methylidynetris.

Further, the compound represented by the following formula may be used as a chromogen.

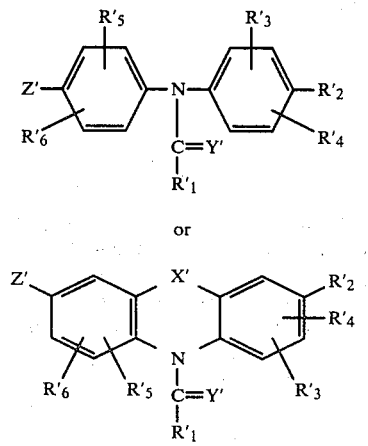

In the formula, $Z'$ represents hydroxyl, amino or substituted amino, $Y'$ represents oxygen atom or sulfur atom, $R'_1$ represents hydrogen, alkyl, alkenyl, aryl, amino or monosubstituted amino, $R'_2$ represents hydrogen, hydroxyl, alkyl, alkenyl, aryl, amino, alkyl-amino or alkoxy, $R'_3$, $R'_4$, $R'_5$ and $R'_6$ represent hydrogen, alkyl, alkenyl, acyl, aryl, halogen, sulfo, nitro, carboxyl, hydroxyl, hydroxyalkyl or alkoxy, $R'_3$ and $R'_4$ or $R'_5$ and $R'_6$ may form alkenylene, $X'$ represents —S—, —O—,

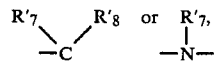

$R'_7$ and $R'_8$ represent hydrogen, alkyl, alkenyl or aryl.

There is a disclosure of this compound as a chromogen in U.S. Patent Application Ser. No. 288,123 filed on July 29, 1981.

In carrying out the determination, the enzymatic reaction is usually carried out at a temperature of 5°–50° C., preferably 25°–40° C. in a buffer solution having a pH of 2–10 and is completed in several minutes.

The chromogen is used in an equimolar amount with hydrogen peroxide or more, preferably 10–1000 mole equivalents. Enzymes are used in a concentration of 0.1–1000 IU/ml, preferably 1–100 IU/ml.

As buffers, phosphate buffer, tris-HCl buffer, succinate buffer, citrate buffer, acetate buffer, etc. may be used in a concentration of 0.005–2 mol/l.

Another aspect of the present invention is to provide a composition for decomposing hydrogen peroxide which comprises Compound (I) and peroxidase. The composition may contain an oxidase and other enzymes or compounds necessary for the determination.

Certain specific embodiments of the invention are illustrated by the following representative examples.

EXAMPLE 1

In this example, 2.0 ml of 0.1 M phosphate buffer (pH 7.3) containing 30 $\mu$M of phenol, 30 mg of Triton X-100, 10 U of peroxidase and 6 U of cholesterol oxidase is poured into three test tubes (A, B and C). 20 $\mu$l of serum is added to test tube (A) and the test tubes are incubated at 37° C. for 10 minutes. Then, 1 ml of 0.1 M phosphate buffer (pH 7.3) containing 1 $\mu$M of 4-AA and 3 U of cholesterol esterase is added to the three test tubes. To test tube (B) is added cholesterol standard solution containing 200 mg/dl cholesterol and to test tube (C) is added 20 $\mu$l of distilled water. The three tubes are incubated at 37° C. for 10 minutes.

After completion of the reaction, the absorbancies of the reaction solutions of tubes (A) and (B) are measured using the solution of tube (C) as a control at 500 nm with double beam spectrophotometer. The content of cholesterol ester in tube (A) is calculated as 156.28 mg/dl.

For comparison, the amount of cholesterol ester in the same serum is determined according to the prior method.

Determination of free cholesterol 3.0 ml of 0.1 M phosphate buffer (pH 7.3) containing 30 $\mu$M of phenol, 30 mg of Triton X-100, 10 U of peroxidase, 6 U of cholesterol oxidase and 1 $\mu$M of 4-AA is poured into three test tubes (A, B and C). Then, 20 $\mu$l of serum is added to tube (A), 20 $\mu$l of cholesterol standard solution containing 200 mg/dl cholesterol is added to tube (B) and 20 $\mu$l of water is added to tube (C). The three tubes are incubated at 37° C. for 10 minutes. The absorbancies of tubes (A) and (B) are measured at 500 nm with double beam spectrophotometer using a solution of tube (C) as a control.

The content of cholesterol in serum is calculated as 44.13 mg/dl.

Determination of total cholesterol

The same procedures as described above are repeated except that 3 U of cholesterol esterase is further added to three test tubes. The content of total cholesterol in serum is calculated as 200.92 mg/dl.

As a result of two experiments, the content of cholesterol ester is calculated as 156.79 mg/dl, which almost agrees with the value of cholesterol ester content obtained by the present method.

EXAMPLE 2

To three test tubes (A, B and C) is poured 2.0 ml of 0.1 M phosphate buffer (pH 6.0) containing 2 μM of N-ethyl-N-(3-methylphenyl)-N'-acetylethylenediamine, 60 mg of Triton X-100, 10 U of peroxidase and 10 U of cholesterol oxidase. 20 μl of serum is added to test tube (A) and the tubes are incubated at 37° C. for 5 minutes. Then, 1.0 ml of phosphate buffer (pH 6.0 ) containing 1 μM of 4-AA and 5 U of cholesterol esterase is added to the tubes (A, B and C). 20 μl of cholesterol standard solution containing 100 mg/dl cholesterol is added to tube (B) and 20 μl of water is added to tube (C). The three tubes are incubated at 37° C. for 5 minutes.

The absorbancies of the reaction solutions are measured at 550 nm and the content of cholesterol ester is calculated as 158.30 mg/dl.

EXAMPLE 3

2 ml of 0.1 M Tris-HCl-buffer (pH 7.5) containing 10 μM of p-chlorophenol, 30 mg of Triton X-100, 20 U of peroxidase and 5 U of choline oxidase is poured into test tubes (A, B and C) and 20 μl of serum is added to tube (A). Thr three tubes are incubated at 37° C. for 5 minutes and 1.0 ml of 0.1 M Tris-HCl-buffer solution (pH 7.5) containing 1 μM of 4-AA and 0.6 U of phospholipase D (EC 3.1.4.4.) is added thereto. 20 μl of choline standard solution containing 300 mg/dl choline as lecithin is added to tube (B) and 20 μl of water is added to tube (C). The three tubes are incubated at 37° C. for 5 minutes and the absorbancies of the reaction solutions in tubes (A) and (B) are measured at 505 nm with double beam spectrophotometer by using the solution of tube (A) as a control.

The content of phospholipid containing choline in molecule is calculated as 172.11 mg/dl.

The determination by prior method is described below.

Determination of free choline in serum 3.0 ml of 0.1 M Tris-HCl-buffer (pH 7.5) containing 10 μM of p-chlorophenol, 30 mg of Triton X-100, 20 U of peroxidase, 5 U of choline oxidase and 1 μM of 4-AA is poured into test tubes (A, B and C). To tube (A) is added 20 μl of serum, to tube (B) is added 20 μl of choline standard solution containing 300 mg/dl choline as lecithin and to tube (C) is added 20 μl of water. The three tubes are incubated at 37° C. for 5 minutes and the absorbancies of the reaction solutions of tubes (A) and (B) are measured at 505 nm with spectrophotometer using the solution of tube (C) as a control. The content of free form of choline is calculated as 13.59 mg/dl.

Determination of total choline

The same procedures as described above are repeated except that 0.6 U of phospholipase D is further added to three test tubes and the content of total choline is calculated as 188.04 mg/dl. The phospholipid is calculated as 174.45 mg/dl, which almost agrees with that obtained by the present method.

EXAMPLE 4

In this example, 2.0 ml of 50 mM phosphate buffer (pH 7.0) containing 5 μM of dimethylaniline, 30 mg of Triton X-100, 40 U of peroxidase and 50 U of glycerol oxidase is poured into three tubes (A, B and C). 20 μl of serum is added to tube (A) and the three tubes are incubated at 37° C. for 10 minutes. Then, 1.0 ml of 50 mM phosphate buffer (pH 7.0) containing 1 μM of 4-AA and 0.5 U of lipoprotein lipase (EC 3.1.1.3.) is added to the three tubes and 20 μl of glycerol standard solution (corresponding to 200 mg/dl triolein) is added to tube (B) and 20 μl of purified water is added to tube (C). The three tubes are incubated at 37° C. for 10 minutes and the absorbancies of the reaction solutions of tube (A) and tube (B) are measured at 550 nm using the reaction solution of tube (C) as a control. The content of neutral lipid in the serum is calculated as 146.19 mg/dl.

The determination by prior method is described below.

Determination of free form of glycerol 3.0 ml of 50 mM phosphate buffer (pH 7.0) containing 5 μmol of dimethylaniline, 30 mg of Triton X-100, 40 U of peroxidase, 50 U of glycerol oxidase and 1 μM of 4-AA is poured into three tubes (A, B and C). Further, 20 μl of serum is added to tube (A), 20 μl of glycerol standard solution described above is added to tube (B) and 20 μl of purified water is added to tube (C). The three tubes are incubated at 37° C. for 10 minutes. The absorbancies of the reaction solutions of tubes (A and B) are measured at 550 nm with double beam spectrophotometer using the reaction solution of tube (C) as a control.

The content of free form of glycerol is calculated as 8.89 mg/dl.

Determination of total glycerol

The same procedures as described above are repeated except that 0.5 U of lipoprotein lipase is further added to three tubes (A, B and C). The content of total glycerol is calculated as 154.46 mg/dl and the content of neutral lipid is calculated as 145.57 mg/dl.

The result of the present method agrees with that of prior method.

EXAMPLE 5

In this example, 100 g of herring roe is bleached at 5° C. for 3 days with hydrochloride solution containing 3% hydrogen peroxide and then is dipped in 1 l of hydrochloride solution containing 20 U/ml catalase at 5° C. for 3 days to decompose hydrogen peroxide. The herring roe contains 2.5 ppm of hydrogen peroxide on the third day of the treatment, 2.5 ppm on the fourth day, 2.4 ppm on the fifth day and 2.4 ppm on the sixth day.

100 g of herring roe treated for 3 days with hydrogen peroxide solution and for 3 days with catalase and containing 2.5 ppm hydrogen peroxide is maintained for 30 minutes in 1 l of solution containing 3 μmol of m-methoxydimethylaniline and 10 U/ml peroxidase, whereby the content of hydrogen peroxide in the herring roe is decreased to less than 0.5 ppm.

EXAMPLE 6

In this example, 2 ml of 0.1 M phosphate buffer (pH 6.5) containing 0.15% Triton X-100, 0.6 mg of phenol, 0.6 mg of semicarbazide hydrochloride, 4 U of pyranose oxidase and 10 U of peroxidase is incubated at 37° C. for 10 minutes. To the mixture is added 20 μl of test serum and the mixture is incubated at 37° C. for 5 minutes. Then, 1 ml of 0.1 M phosphate buffer (pH 6.5) containing 20 mg of maltopentaose, 0.2 mg of 4-AA and 20 U of peroxidase is added to the mixture and the resulting mixture is incubated at 37° C. for 3 minutes. The absorbancy of the reaction solution is measured at 500 nm.

The same procedures as described above are repeated on the standard serum as a sample. The amylase activity in the test serum is determined as 98 U.

EXAMPLE 7

In this example, 2 ml of 0.05 M phosphate buffer (pH 6.5) containing 0.6 mg of magnesium chloride, 6.9 mg of thiamine pyrophosphate, 6 U of pyruvate oxidase, 10 U of oxaloacetate decarboxylase, 0.1 mg of phenol and 10 U of peroxidase is incubated at 37° C. for 10 minutes. To the mixture is added 50 μl of test serum and the mixture is incubated at 37° C. for 5 minutes. Then, 1 ml of 0.05 M phosphate buffer (pH 6.5) containing 200 mg of L-alanine, 5.1 mg of α-keto-glutaric acid, 0.05 mg of the compound represented by the formula below and 20 U of peroxidase is added to the mixture and the resulting mixture is incubated at 37° C. for 2 minutes. The absorbancy of the reaction solution is measured at 660 nm.

The same procedures as described above are repeated on the standard serum as a test sample and the glutamate pyruvate transaminase activity in the test serum is calculated as 60 IU/l.

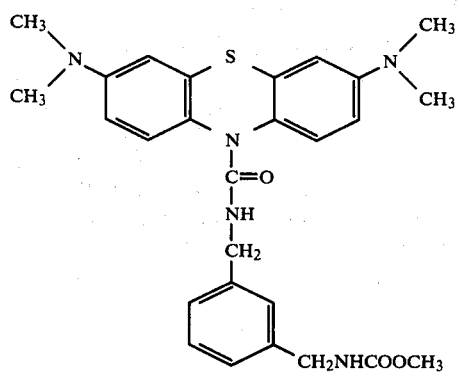

What is claimed is:

1. A method for determination of an analyte which can be converted by the action of an enzyme (B) to the compound (A) which can be directly oxidized by the action of an oxidase capable of oxidizing the compound (A), which comprises the following steps:
   (1) compound (A) in the original sample is oxidized by the action of the oxidase to form hydrogen peroxide;
   (2) the resultant hydrogen peroxide is decomposed by adding peroxidase and a compound represented by the formula (I)

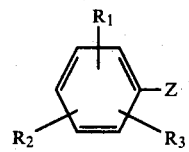

wherein Z represents OH or $NR_4 \cdot R_5$ wherein $R_4$ and $R_5$ are the same or different and represent hydrogen atom, alkyl, substituted alkyl or acyl, and $R_1$, $R_2$ and $R_3$ are the same or different and represent hydrogen atom, halogen atom, alkyl, alkoxy, amino, nitro, carboxyl or sulphonyl;
   (3) the analyte is converted to compound (A) by the action of enzyme (B);
   (4) the resultant compound (A) is oxidized by the action of the oxidase to form hydrogen peroxide; and
   (5) the resultant hydrogen peroxide is determined by a known method.

2. The method according to claim 1, wherein Z is OH.

3. The method according to claim 1, wherein Z is $NR_4 \cdot R_5$.

4. The method according to claim 1, wherein said compound is selected from the group consisting of phenol, 2,4-dichlorophenol, p-chlorophenol, 2,4-dibromophenol, p-bromophenol, 2,3-dichlorophenol, 2-nitrophenol, 3-nitrophenol, 2-aminophenol, 3-aminophenol, aniline, 2-bromoaniline, 3-bromoaniline, 2-chloroaniline, 3-chloroaniline, o-toluidine, m-toluidine, dimethylaniline, diethylaniline, o-phenylenediamine, N,N-p-phenylenediamine, o-anisidine, m-anisidine, o-cresol, m-cresol, 2-methyl-2,6-dinitrophenol, 2-methoxy-5-nitroaniline, 2-methyl-5-nitroaniline, 3,5-dihydroxytoluene, 3-methoxyphenol, 2-amino-5-methylphenol, 2-hydroxy-3-methylbenzoic acid, 2-hydroxyphenylacetic acid, 2,3-dimethylphenol, 2,5-dimethylphenol, 2-ethylphenol, 3-ethylphenol, 2-methoxymethylphenol, 2,3-dimethylaniline, 2,5-dimethylaniline, 3,5-diethylaniline, 3-(dimethylamino)phenol, 3-methoxy-N,N-dimethylaniline, N,N-diethyl-1,3-phenylenediamine, 3,5-dimethyl-1,2-phenylenediamine, and N-ethyl-N-(3-methylphenyl)-N'-acetylethylenediamine.

5. The method according to claim 1, wherein said determination of hydrogen peroxide is carried out by adding peroxidase and chromogen to form a pigment and measuring the absorbancy of the reaction solution colored by the formation of the pigment.

6. The method according to claim 5, wherein said analyte is selected from cholesterol ester, triglyceride, phospholipid, sialocompound and creatinine.

7. The method according to claim 5, wherein said analyte is cholesterol ester, compound (A) is cholesterol, enzyme (B) is cholesterol esterase and oxidase is cholesterol oxidase.

8. The method according to claim 5, wherein said analyte is triglyceride, compound (A) is glycerol, enzyme (B) is lipoprotein lipase and oxidase is glycerol oxidase.

9. In a method for the determination of activity of an enzyme in a sample by the following steps:
   (1) the substrate for the enzyme is added to the sample to convert the substrate to a compound (A) which can be directly oxidized by the action of the oxidase capable of oxidizing the compound (A), (2) the oxidase is added to the enzymatic reaction mixture to oxidize the compound (A) to form hydrogen peroxide, (3) the formed hydrogen peroxide is determined by a known method, the improvement comprising decomposing compound (A) in the original sample prior to the determination; said decomposition being carried out by adding the oxidase to oxidize compound (A) in the original sample, whereby hydrogen peroxide is formed, and adding a compound represented by the formula (I)

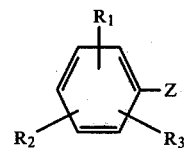

wherein Z represents OH or $NR_4.R_5$ wherein $R_4$ and $R_5$ are the same or different and represent hydrogen atom, alkyl, substituted alkyl or acyl, and $R_1$, $R_2$ and $R_3$ are the same or different and represent hydrogen atom, halogen atom, alkyl, alkoxy, amino, nitro, carboxyl or sulphonyl, and peroxidase to decompose the formed hydrogen peroxide, whereby a non-coloring compound is formed.

* * * * *